(12) United States Patent
Gao et al.

(10) Patent No.: US 8,246,668 B2
(45) Date of Patent: Aug. 21, 2012

(54) CONTROLLABLE INFRARED BIOEFFECT SYSTEM

(75) Inventors: Xinghua Gao, Shenyang (CN); Ruiqun Qi, Shenyang (CN); Feng Xu, Shenyang (CN); Hongduo Chen, Shenyang (CN)

(73) Assignee: The First Hospital of China Medical University, Shengyang (CN)

( * ) Notice: Subject to any disclaimer, the term of this patent is extended or adjusted under 35 U.S.C. 154(b) by 287 days.

(21) Appl. No.: 12/742,811

(22) PCT Filed: Apr. 14, 2009

(86) PCT No.: PCT/CN2009/071260
§ 371 (c)(1),
(2), (4) Date: May 13, 2010

(87) PCT Pub. No.: WO2010/072061
PCT Pub. Date: Jul. 1, 2010

(65) Prior Publication Data
US 2010/0324634 A1 Dec. 23, 2010

(30) Foreign Application Priority Data

Dec. 23, 2008 (CN) .......................... 2008 1 0230063

(51) Int. Cl.
*A61N 5/06* (2006.01)
(52) U.S. Cl. ................................. 607/90; 607/88; 606/9
(58) Field of Classification Search .................... 607/90, 607/88; 606/9
See application file for complete search history.

(56) References Cited

U.S. PATENT DOCUMENTS

| 5,531,740 A * | 7/1996 | Black ................................. 606/9 |
| 8,133,180 B2 * | 3/2012 | Slayton et al. ................. 600/439 |
| 2006/0116562 A1 * | 6/2006 | Acosta et al. ................. 600/316 |

FOREIGN PATENT DOCUMENTS

| CN | 2559366 Y | 7/2003 |
| CN | 1666791 A | 9/2005 |
| CN | 1861214 A | 11/2006 |
| KR | 2002008734 A | 11/2002 |

* cited by examiner

Primary Examiner — Kinam Park

(57) ABSTRACT

The present invention belongs to the technical field of infrared research and application in biomedicine. In particular, it refers to an apparatus of bio-effect system with the use of controllable infrared wave. The invention includes a shell (16); a infrared source (1) inside of the shell (16), the first group of filter mounting plate (2), convex lens (3), concave lens (4), the second groups of filter mounting plate (5), cable receptor device (6) and execution end (18); the first group of filter mounting plate (2) and the second group of filter mounting plate (5) are in line with the central axis; the described convex lens (3) is installed between the infrared source (1) and concave lens (4); the described first group of filter mounting plate (2) and the second group of filter mounting plate (5) are located between the concave lens (4) and the cable receptor device (6); the described second group of filter mounting plate (2) is installed with the first filter (23); the second group of filter mounting plate (5) is installed with the second filter (7). The invention is simple in structure. It is used to irradiate the test material, by selecting certain wavelength of IF-IR.

16 Claims, 7 Drawing Sheets

CONTROLLABLE INFRARED BIOEFFECT SYSTEM

TECHNICAL FIELD

The present invention belongs to the technical field of infrared research and application in biomedicine. In particular, it refers to an apparatus of bio-effect system with the use of controllable infrared wave.

BACKGROUND TECHNIQUE

From the clinical point of view, many kinds of physical options are available for the treatment of neoplastic skin diseases. For example, laser-therapy, cryotherapy, thermotherapy, electrocautery, etc. The treatment of neoplastic lesions is mostly ablative, for example, carbon dioxide laser is use to cauterize the warts, liquid nitrogen is used to freeze Bowen disease (precancerous lesion) and etc. These methods may cause scarring, are poorly tolerated during the procedures. Non-ablative method with good efficiency is highly expected.

In the search of non-ablative treatment methods, the National Key Laboratory of the Health Ministry, at the State Key Department of Dermatology of Chinese Medical University investigated and found that infrared heading has significant effect on curing some certain kinds of skin diseases, some results has been published in academic journals. More importantly, by employing molecular biology and immunology methods, they found that appropriated length and temperature of the infrared heating can influence immune cells of the skin, such as stimulating the migrational maturation of Langerhans cells, promoting cell apoptosis and etc. The effect on promoting establishment of specific immune response was observed in that there were concomitant elimination of targeted virus harboring lesion as well as non-targeted lesions, during the local infrared heating treatment.

Figure 11:
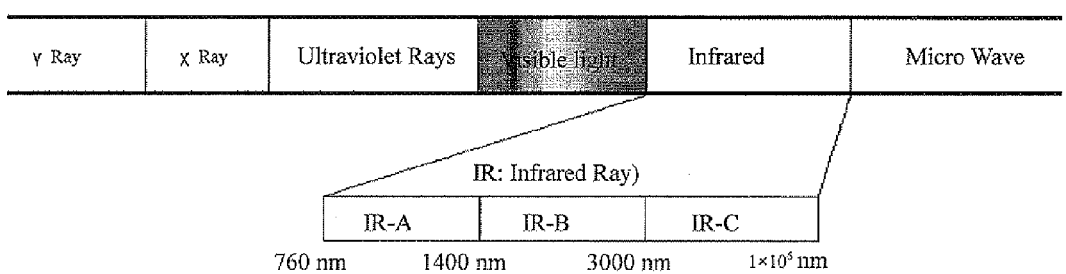
Figure 12:
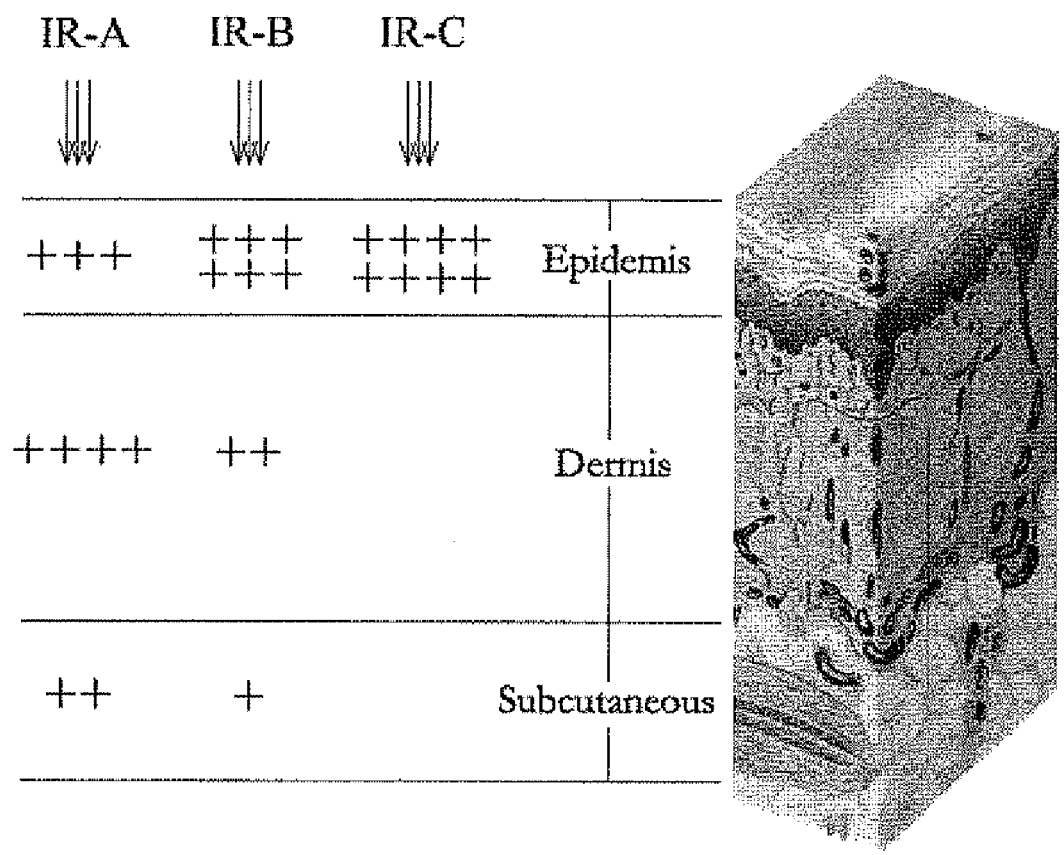

Different lengths of wave can reach to different layers of skin. The absorption rates of IR in each layer of skin depend on the wavelength of the IR. Therefore, biological effects of IR on different layers of skin are different. Physically, IR is divided into three ranges of Near-IR, Mid-IR and Far-IR. While by the sense of bio-effect, IR is divided into different bands according to its potential to reach the depths of skin. The bio-Effect IR spectrum and the IR absorption rates of each layer of skin are shown in FIGS. 11 and 12.

IR-Technique is being applied to a broad range of fields, including measuring, monitoring, photographing and physiotherapy. By virtue of its heating effect, infrared radiation has been Used in health care. The IR-products available in the market for heating are IR heater and heating bandage. There has been a lack in the specific control of wavelength, temperature and illuminated area of IR, in those marketed IR-products. An IR-product with characteristics of controllable specific wave length, energy output, target area, would be needed in health care research and possibly treating some skin diseases.

SUMMARY OF THE INVENTION

The contents of the invention are to provide a controllable IR bio-effect system. The system has characteristics of controllable specific wavelength of IR, energy output, and targeting area.

To achieve the above-mentioned purposes, the details of the inventions are as following:

The controllable infrared bio-effect system includes a shell (16), which contains a infrared source (1), the first group of filter mounting plate (2) convex lens (3), concave lens (4), the second group of filter mounting plate (5), cable receptor device (6) and execution end (18); the first group of filter mounting plate (2) and the second group of filter mounting plate (5) are in line with the central axis, the described convex lens (3) is installed between the infrared source (1) and concave lens (4); the described first group of filter mounting plate (2) and the second group of filter mounting plate (5) are located between the concave lens (4) and the cable receptor device (6); the described second group of filter mounting plate (2) is installed with the first filter (23); the second group of filter mounting plate (5) is installed with the second filter (7); the first filter (23) is in the same axis with second filter (7); the first group of filter mounting plate (2), convex lens (3), concave lens (4), and second group of filter mounting plate (5) are parallely installed; the output end of the cable receptor device (6) is through the cable (8) and connected with the execution end (18).

The first filter (23) is to filter the UV rays and visible lights emitted by the infrared source (1);

The concave lens (4) is to make parallel the spotted IR beam by convex lens (3);

The second filter (7) is used to receive the desired wavelength of infrared radiation;

The cable receptor device (6) is to receive the beam emitted form the second filter (7), and transmit the beam to the execution end (18) through the cable (8).

As one of the optimal option, the invention has a third filter (9) in the second group of filter mounting plate (5); an optical channel (24) is installed in the first group of filter mounting plate (2); the optical channel (24) is in the same axis with the third filter (9); the third filter (9) is used to receive the desired wavelength of infrared radiation emitted faun the source (1); the cable receptor device (6) is used to receive the beam, and transmit the beam to the execution end (18) through the cable (8).

As one of the optimal option, the invention has two parallel binary lenses A (10) and B (11). The two binary lenses A (10) and B (11) are installed in the second group of filter mounting plate (5) in an angle of 45°, respectively; install an optimal channel B (13) in the place opposite to binary lens B (11) on the second group of filter mounting plate (5); install a fourth filter (25) in the first group of filter mounting plate (2); the forth filter (25) is fixed in the same axis with the binary lens A (10); the binary lens B (11) receives the beams emitted from the concave lens (4) and the fourth filter (25), and then the produced beam is transmitted to cable receptor (6) through binary lens B (11) and optimal channel (13).

The invention is characterized by equipping with a control system. The control system includes a CPU, a display part, a drive and temperature signal collector (19). The temperature signal collector (19) is adapted with the execution end (18). The output port of the CPU is connected with the input port of the display. The output port of the CPU is connected with the output port of the IR source (1). The port of the temperature signal collector (19) is connected with the port of the CPU.

The temperature signal collecting part is used to collect the temperature signals and related data, then send them back to the CPU.

The drive is used to drive IR source (1).

The invention is installed with drive motor (14) and rack (20) which are fixed inside the shell (16) of the invention. A driven wheel (15) is fixed in the axis between the first group of filter mounting plate (2) and the second group of filter mounting plate (5). The first and second group of filter mounting plates (2) and (5) can rotate around the rack. The output axis of the drive motor (14) is connecting with the driven wheel (15).

A fan (17) is fixed inside of the shell (16).

The vent(s) (21) on the execution end (18) are in retractable structure.

The transmission rates of binary lenses A (10) and B (11) are greater-than-or-equal to 85% when the wavelength of IR transmitting the lenses is from 1400 nm to 2500 nm. The transmission rates of binary lenses A (10) and B (11) are lesser-than-or-equal to 5% when the wavelength of IR transmitting the lenses is from 800 nm to 1300 nm.

The transmission rates of the second filter (7) are greater-than-or-equal to 85% when the wavelength of IR transmitting the lenses is from 1600 nm to 2600 nm. The transmission rates of the second filter are greater-than-or-equal to 85% when the wavelength of IR transmitting the lenses is from 1400 nm to 2500 nm.

The transmission rate of the third filter (9) is greater-than-or-equal to 85% when the wavelength of IR transmitting the lenses is from 3000 nm to 5000 nm. The transmission rate of the third filter is lesser-than-or-equal to 5% when the wavelength of IR transmitting the lenses is from 200 nm to 2700 nm.

Compared with the available products, the invention has the advantages featured by:
1. The selectable wave length of IR by this invention is adopted for the bioavailability of different skin compartment. The characterized features of the invention would help in studying the specific functions of IR in different layers of skin.
2. Different specific wavelength of IR could be generated by the invention; this feature is achieved by adopting filters for different wavelength of IR.
3. The invention is designed to generate stable and measurable out put of heat on the tested subject, in an adjustably fixed time.
4. The invention is designed to have no direct contact with the heated subject, to avoid the possibility of transmitting diseases between different subjects.
5. In accordance to the size of the target, the optical spots are adjustable.
6. The information of the patients can be stored. The treatment parameters can be saved.

FIGURE DESCRIPTIONS

The invention will now be described in figures so that it may be more fully understood. The scope of the invention is not intended to be limited to the details below.

Figure 1:
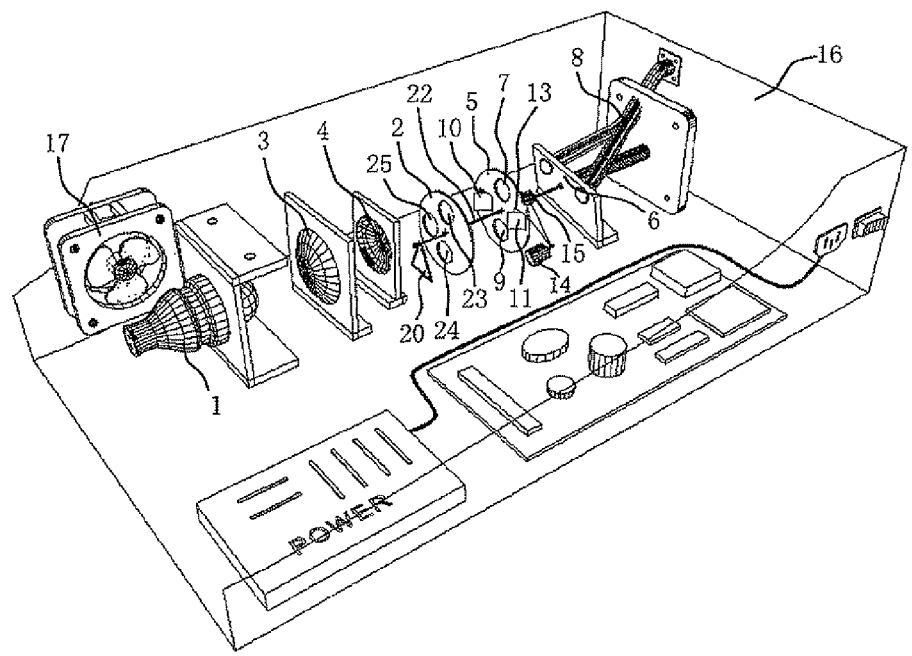

FIG. 1: Diagram of the whole structure in the present invention.

Figure 2:
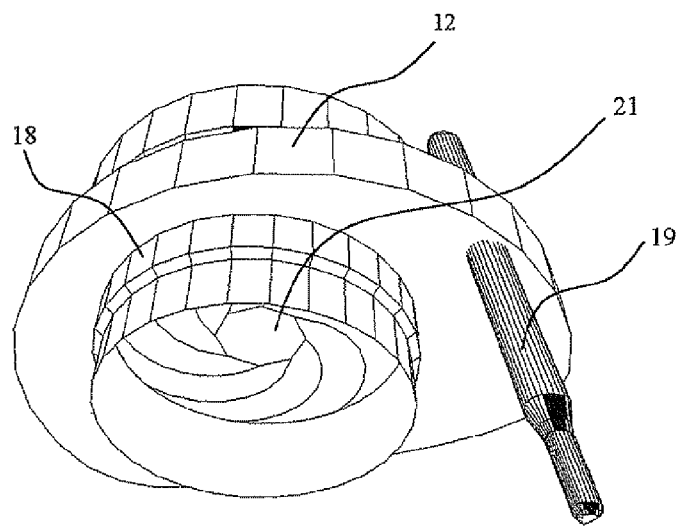

FIG. 2: Diagram of the execution end in the present invention.

Figure 3:
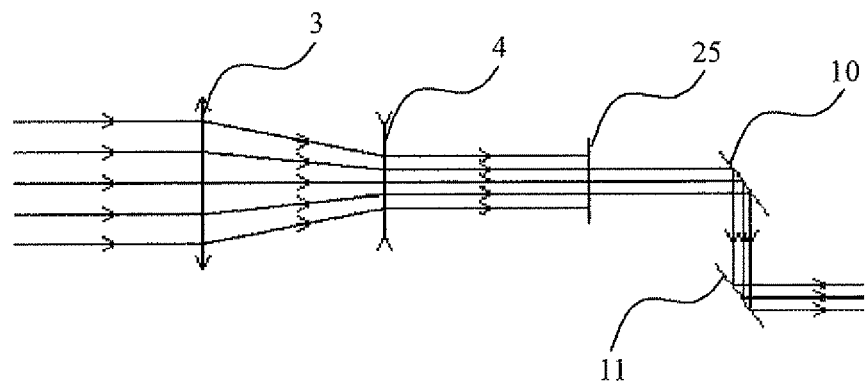
Figures 1, 4:
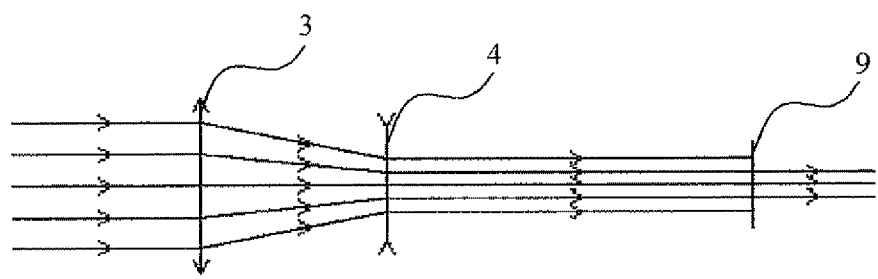
Figures 2, 4:
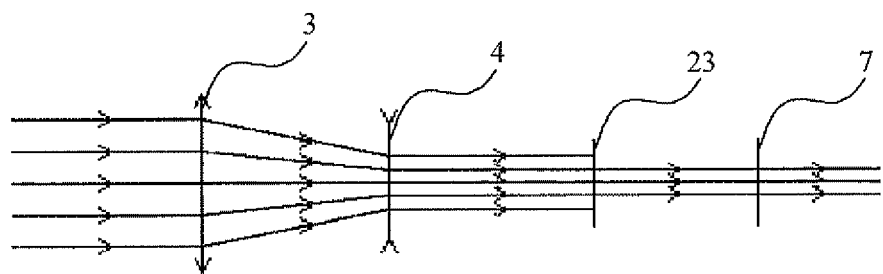

FIG. 3: diagram of the light-path for an operational method in the present invention FIG. 4-1: Diagram of the light-path for an alternative operational method in the present invention FIG. 4-2: Diagram of the light-path for another alternative operational method in the present invention FIG. 5-1: Diagram of the schematic circuits of the control system in the present invention.

Figures 1, 5:
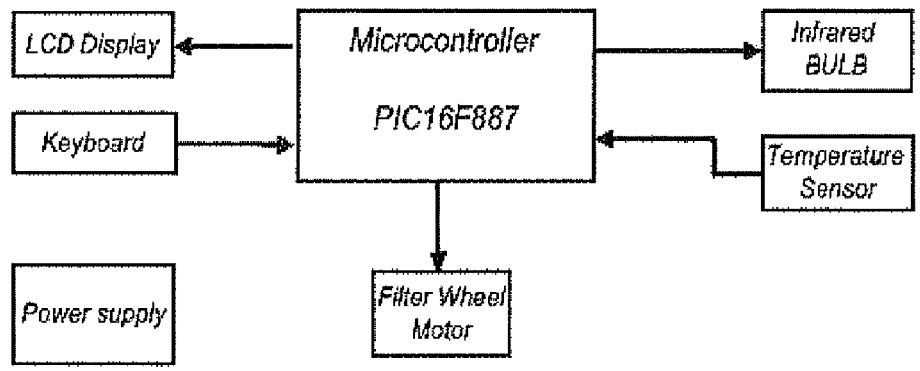
Figures 2, 5:
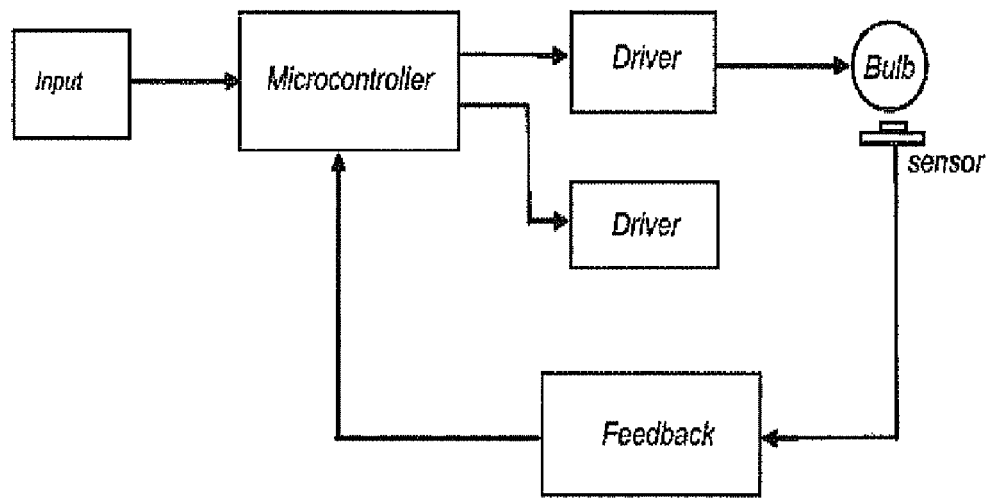

FIG. 5-2: Diagram of the schematic circuits for the driven part of the control system in the present invention.

Figure 6:
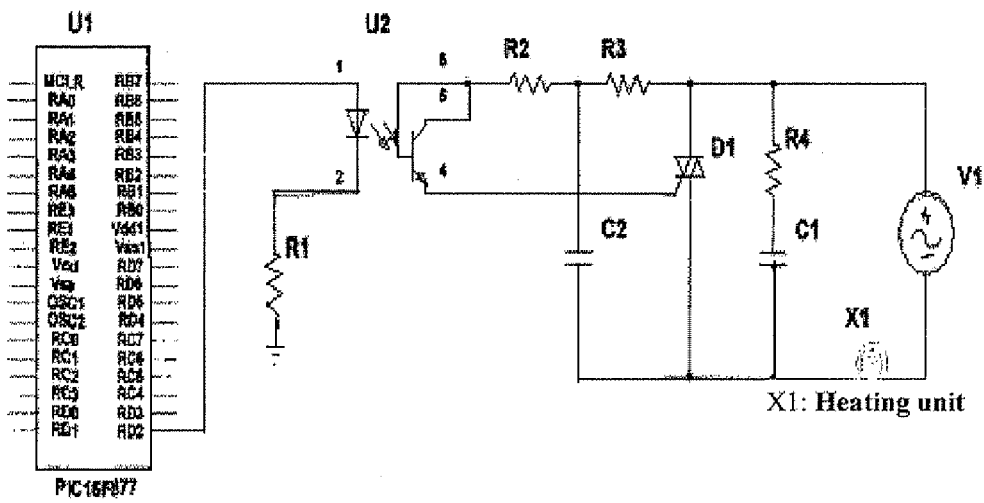

FIG. 6: Diagram of the concrete circuits for the driving part of the control system in the present invention.

Figure 7:
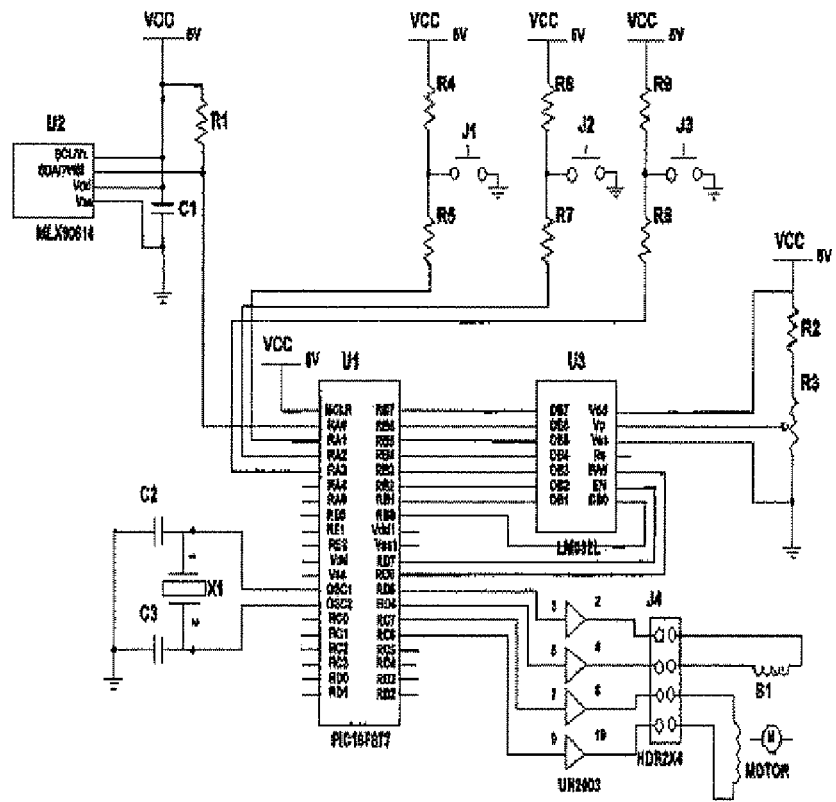

FIG. 7: Diagram of the concrete circuits for the display part of the control system in the present invention.

Figure 8:
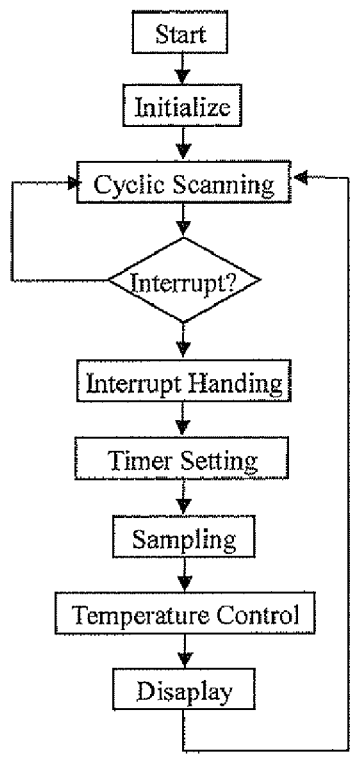

FIG. 8: Flow chart for the main program of the control system in the present invention.

Figure 9:
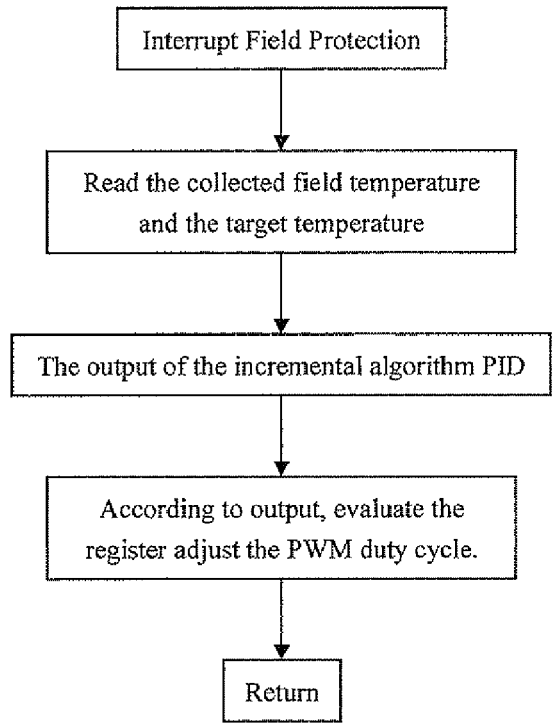

FIG. 9: Flow chart for the subprogram of temperature control system in the present invention.

Figure 10:
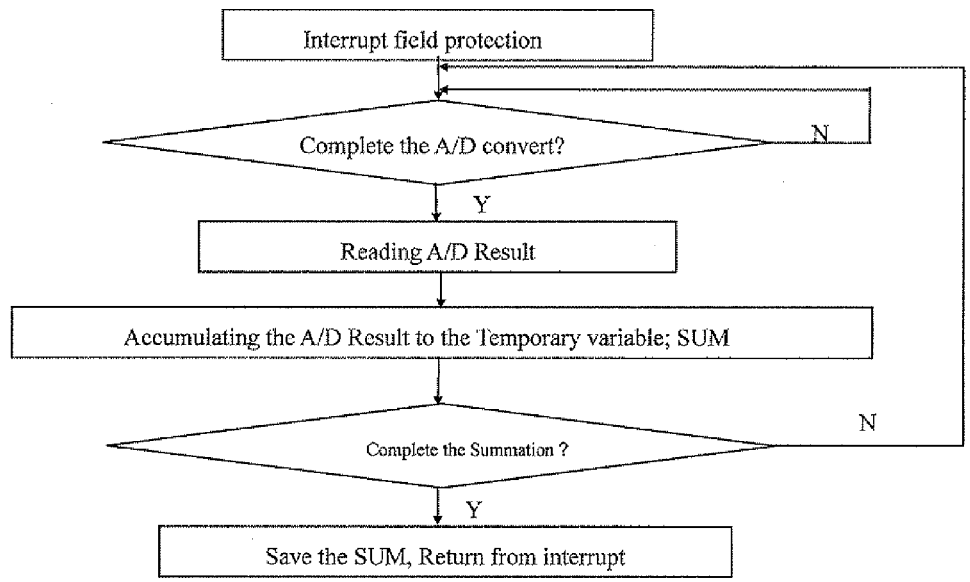

FIG. 10: Flow chart for the subprogram of heating control system in the present invention.

FIG. 11: Diagram of the range of infrared spectrum

FIG. 12: Diagram of depths and absorption rates of skin when illuminated by different wavelength of IR

IMPLEMENTATION DETAILS

As FIGS. 1 and 2 shows, the controllable infrared wave bio-effect system includes shell (16), in which an infrared source (1), the first group of filter mounting plate (2), convex lens (3), concave lens (4), the second group of filter mounting plate (5), cable receptor device (6) and execution end (18), are installed. The first group of filter mounting plate (2) and the second group of filter mounting plate (5) are in a common central axis. The described convex lens (3) is installed between the infrared source (1) and concave lens (4); the described first group of filter mounting plate (2) and the second group of filter mounting plate (5) are located between the concave lens (4) and the cable receptor device (6); the described second group of filter mounting plate (2) is installed with the first filter (23); the second group of the filter mounting plate (5) is installed with the second filter (7); the first filter (23) is in the same axis with second filter (7); the first group of filter mounting plate (2), convex lens (3), concave lens (4), and second group of filter mounting plate (5) are parallelly installed; the output end of the cable receptor device (6) is through the cable (8) and connected with the execution end (18); the first filter (23) is to filter the UV rays and visible lights emitted by the infrared source (1); the concave lens (4) is to make parallel the spotted IR beam emitted from the convex lens (3); the second filter (7) is used to receive the desired wavelength of IR; the cable receptor device (6) is to receive the beam emitted form the second filter (7), and transmit it to the execution end (18) through the cable (8).

The base plate of the first filter (23) is Φ30±1×3±0.2 mm (HB780) in size, without coating. The base plate of the second filter (7) is Φ30±1×5±0.2 mm (IR-B780) in size. When the wavelength of IR through the second filter (7) is within the range of 1600~2600 nm, the transmittance of the light is equal or greater than 85%; when the wavelength of IR through the second filter (7) is within the range of 750~1400 nm, the transmittance of the light is lesser-than-or-equal to 5%.

To increase the selective band of IR, a third filter (9) is installed on the second group of filter mounting plate (5) in the invention. The optical channel (24) is sharing the same axis with the first group of filter mounting plate (2). The third filter (9) is used to intercept the desired wavelength of IR. The cable receptor device (6) is used to receive light wave from the third filter (9), and then transmits it to the execution end (18) through cable (8).

The base plate of the third filter (9) is a piece of germanium-coating glass of Φ30±1×2±0.2 mm. When the wavelength of IR through the third filter (9) is from 3000 nm to 5000 nm, the transmittance of the light is to be equal or greater than 85%. When the wavelength range of IR through the third filter (9) is from 200 nm to 2700 nm, the transmittance of the light is lesser-than-or-equal to 5%.

In order to increase the number of selective band within IR, two pair of parallel binary lenses A (10) and B (11) are installed in the system. The two binary lenses A (10) and B (11) are at 45° angle with the second group of filter mounting plate (5). The optical channel B (13) is located at the binary lens B (11) of the second group of filter mounting plate (5). A fourth filter (25) is installed at the first group of filter mounting plate (2). The fourth filter (25) is sharing the same axis with the binary lens A (10). The binary lens A (10) receives the beam from the concave lens (4) and the fourth filter (25); the light beam is transmitted to the cable receptor device (6) though the binary lens B (11) and the optical channel B (13). See FIG. 3 for the Light-path diagram.

The base plate of the fourth filter (25) is Φ30±1×3±0.2 mm (IR-B780) in size, without coating. The base plate of the two binary lenses A (10) and B (11) is Φ30±1×5±0.2 min (IR-A, coated with B270). When the wavelength of the IR is between from 1400 nm to 2500 nm, the transmittance of the two binary lenses A (10) and B (11) is greater or equal to 85%. When the wavelength of the IR is from 800 nm to 1300 nm, the transmittance of the two binary lenses A (10) and B (11) is lesser or equal to 15%. As shown in the FIGS. 11 and 12, the wavelength of the IR from the two binary lenses A (10) and B (11) is within the range of IR-A. The light-path diagram of the invention is shown in FIG. 3.

To increase the accuracy of IR control, the invention is installed with a control system. As shown in FIGS. 5-1, 5-2, 6 and 7. The control system includes a CPU, a display part, a drive part and a temperature signal collecting part (19). The temperature signal collecting part (19) is fixed at the execution end (18). The output end of the CPU is connected with the input end of the display part. The output end of the CPU is connected with the input end of the infrared source (1) through the drive part. The port of the temperature signal collecting part (19) is connected with the port of the CPU.

The temperature signal collecting part (19) is used to collect temperature signal, and sent these data to the CPU for processing.

The CPU is responsible for processing the data and sending directions.

The drive part is used to drive the infrared source (1).

To select the JR within certain wave band, a drive motor (14) and its rack (20) is installed inside the shell (16) of the invention. A driving wheel is fixed in the middle axis (22) which is shared by the first group of filter mounting plate (2) and the second group of filter mounting plate (5). Both groups of the filter plate can rotate around the rack (20). The output shaft of the drive motor (14) is connected with the driven shaft of the drive motor (14). The output shaft of the drive motor (14) transmits the power to the driven gear (15), by a belt drive or a gear drive.

As shown in FIG. 1. To make the temperature condition within favorable range, a fan (17) is fixed inside of shell (16). A temperature control device is fixed in the shell to start the fan (17). When the temperature of the invention is higher than the fixed point, the fan (17) will start automatically. When the temperature of the invention is lower than the fixed point, the fan (17) will stop automatically.

As shown in FIG. 2, the vent(s) (21) on the execution end (18) are retractable in structure. The radiation controller (12) could rotate around the execution end (18) to change radiation area. The radiation controller could be like the aperture adjustment of a camera.

As shown in the Circuit diagram 4-1, the IR pass trough the optical channel (24) and the third filter (9).

As shown in the Circuit diagram 4-1, the IR pass through the first filter (23) and the second filter (7).

The transmission rates of binary lenses A and B are greater-than-or-equal to 85% when the wavelength of IR transmitting the lenses is from 1400 nm to 2500 nm. The transmission rates of binary lenses A and B are less-than-or-equal to 5% when the wavelength of IR transmitting the lenses is from 800 nm to 1300 nm.

The transmission rate of the second filter is greater-than-or-equal to 85% when the wavelength of IR transmitting the filter is from 1600 nm to 2600 nm. The transmission rate of the second filter is lesser-than-or-equal to 5% when the wavelength of IR transmitting the filter is from 750 nm to 1400 nm.

The transmission rate of the third filter is greater-than-or-equal to 85% when the wavelength of IR transmitting the filter is from 3000 nm to 5000 nm. The transmission rate of the third filter is lesser-than-or-equal to 5% when the wavelength of IR transmitting the filter is from 200 nm to 2700 nm.

The parameters of the two types of lenses in the invention The convex lens and concave lens used in the invention are all IR Calcium Fluoridated.

The parameters of Four Types of Filters in the invention
I. Base Plate: 3 types are as following:
   Φ30±1×3±0.2 mm (HB780), without coating;
   Φ30±1×5±0.2 mm (B270), coated;
   Φ30±1×2±0.2 mm (germanium glass), coated;
II. The coated filters are coated on a single-side. The transmittance are as following:
   1) IR-A Filter
   At 45° angle, when collecting the reflected light:
   1400-2500 nm T≧85%
   800-1300 nm T≦5%
   2) IR-B Filter
   At 0° angle:
   1600-2600 nm T≧85%
   750-1400 nm T≦5%
   3) IR-C Filter
   At 0° angle:
   3000-2600 T≧85%
   750-1400 nm T≦5%
III. Coating Materials: $TIO_2/SIO_2$, $GeO_2/ZnS$, coated with multilayer.
VI. Instruction for use:
   Type I: IR-A Filter is composed of three sets of filters.
   a) Φ30×3 mm (HB780); 1 set
   In front of the light source, at 0° angle. It is used to filter the violet and visible light.
   b) Φ30×5 mm (IR-A coated with B270); 2 sets
   Behind the HB780, at 45° angle.
   Type II. IR-B Filter is composed of two sets of filters.
   a) Φ30×3 mm (HB780); 1 set
   In front of the light source, at 0° angle. It is used to filter the violet and visible light.
   b) Φ30×5 mm (IR-B coated with B270); 1 set
   Behind the HB780, at 0° angle.
   Type III: IR-C Filter is composed of one set of filter.
   a) Φ30×3 mm IR-C germanium coated glass); 1 set at 0° angle;

| Parameters of three types of coated filters | | | | | |
|---|---|---|---|---|---|
| Coated IR-A | | Coated IR-B | | Coated IR-C | |
| TIO2 | 23.28 | TIO2 | 36.16 | GeO2 | 382.83 |
| SIO2 | 279.51 | SIO2 | 198.48 | ZnS | 97.88 |
| TIO2 | 76.80 | TIO2 | 71.88 | GeO2 | 146.02 |
| SIO2 | 199.52 | SIO2 | 142.77 | ZnS | 147.98 |
| TIO2 | 90.86 | TIO2 | 85.95 | GeO2 | 31.99 |
| SIO2 | 91.77 | SIO2 | 131.48 | ZnS | 146.51 |
| TIO2 | 74.13 | TIO2 | 86.11 | GeO2 | 90.50 |

-continued

Parameters of three types of coated filters

| Coated IR-A | | Coated IR-B | | Coated IR-C | |
|---|---|---|---|---|---|
| SIO2 | 151.67 | SIO2 | 110.43 | ZnS  | 2.11 |
| TIO2 | 105.67 | TIO2 | 77.81  | GeO2 | 107.48 |
| SIO2 | 165.44 | SIO2 | 145.73 | ZnS  | 145.83 |
| TIO2 | 71.07  | TIO2 | 93.84  | GeO2 | 111.13 |
| SIO2 | 151.54 | SIO2 | 145.95 | ZnS  | 2.29 |
| TIO2 | 88.57  | TIO2 | 73.29  | GeO2 | 66.59 |
| SIO2 | 165.12 | SIO2 | 130.90 | ZnS  | 196.41 |
| TIO2 | 77.85  | TIO2 | 83.89  | GeO2 | 102.70 |
| SIO2 | 117.40 | SIO2 | 136.41 | ZnS  | 213.80 |
| TIO2 | 92.95  | TIO2 | 77.00  | GeO2 | 109.81 |
| SIO2 | 1.49   | SIO2 | 137.83 | ZnS  | 174.36 |
| TIO2 | 107.81 | TIO2 | 104.41 | GeO2 | 92.43 |
| SIO2 | 1.30   | SIO2 | 1.41   | ZnS  | 204.80 |
| TIO2 | 90.13  | TIO2 | 114.50 | GeO2 | 134.57 |
| SIO2 | 167.74 | SIO2 | 173.36 | ZnS  | 219.33 |
| TIO2 | 107.36 | TIO2 | 95.08  | GeO2 | 131.64 |
| SIO2 | 199.11 | SIO2 | 153.03 | ZnS  | 297.27 |
| TIO2 | 120.67 | TIO2 | 104.35 | GeO2 | 136.14 |
| SIO2 | 205.32 | SIO2 | 3.66   | ZnS  | 236.17 |
| TIO2 | 105.81 | TIO2 | 119.90 | GeO2 | 179.44 |
| SIO2 | 168.53 | SIO2 | 3.68   | ZnS  | 274.07 |
| TIO2 | 94.32  | TIO2 | 103.78 | GeO2 | 151. |
| SIO2 | 1.45   | SIO2 | 148.59 | ZnS  | 264.89 |
| TIO2 | 115.99 | TIO2 | 98.80  | GeO2 | 157.39 |
| SIO2 | 226.61 | SIO2 | 0.95   | ZnS  | 285.51 |
| TIO2 | 125.77 | TIO2 | 123.36 | GeO2 | 145.56 |
| SIO2 | 223.37 | SIO2 | 215.68 | ZnS  | 6.57 |
| TIO2 | 149.73 | TIO2 | 140.14 | GeO2 | 38.45 |
| SIO2 | 202.13 | SIO2 | 199.45 | ZnS  | 405.98 |
| TIO2 | 140.91 | TIO2 | 161.68 | | |
| SIO2 | 259.51 | SIO2 | 199.74 | | |
| TIO2 | 114.37 | TIO2 | 143.13 | | |
| SIO2 | 242.57 | SIO2 | 232.98 | | |
| TIO2 | 161.71 | TIO2 | 137.48 | | |
| SIO2 | 174.53 | SIO2 | 223.72 | | |
| TIO2 | 150.64 | TIO2 | 131.84 | | |
| SIO2 | 264.81 | SIO2 | 259.00 | | |
| TIO2 | 106.15 | TIO2 | 117.27 | | |
| SIO2 | 205.43 | SIO2 | 193.06 | | |
| TIO2 | 234.24 | TIO2 | 221.32 | | |
| SIO2 | 57.54  | SIO2 | 80.88  | | |
| TIO2 | 190.22 | TIO2 | 178.37 | | |
| SIO2 | 428.91 | SIO2 | 413.31 | | |

The general design of the temperature measurement system and heating control system are shown in FIG. 5-1. The control system include field temperature collection, real-time temperature display, parameter set for heating control, output control for heating circuit, motor drive for filter wheel, etc.

The temperature circuits convert the field temperature to digital signal and transferred to the MCU (Micro-Controller Unit). The MCU then calculates the real-time control variable using the field temperature and target temperature set by the user, according to the embedded program of incremental algorithm PID. The control variable can be used to drive and regulate the heating circuit, and trace the target temperature set by the user. All running status of the system can be shown in the LCD. The system control block diagram is shows in FIG. 5-1; FIG. 5-2 shows the drive part of the system.

System Control Algorithm

The system applies the method of Pulse Width Modulation (referred to as the PWM) which is based on the incremental form of the PID algorithm—the duty cycle of the PWM modulation is obtained by calculating the incremental form of the PID algorithm. The output of the PID algorithm is calculated by the following formula:

$$\Delta U_n = Kp[(e_n - e_{n-1}) + (T/T_i)e_n - (T_d/T)(e_{n-2}e_{n-1} + e_{n-2})]$$

In the above formula, the en, en−1, en−2 are the deviation scores of the sqrt[n], sqrt[n−1] and sqrt[n−2]. The Kp, $T_i$ and $T_d$ are the scale factor, integral coefficient and derivative coefficient respectively. T is the sampling period.

The MCU periodically calculates the deviation of the field temperature and the target temperature set by user during the time of T, and then put it into the PID algorithm. The duty cycle of the PWM modulation is calculated by the output of the formula. The power of the heating circuit is decided by the duty cycle of the PWM modulation. When the deviation of the field temperature and the set temperature is high, then the duty cycle is big and lead to the power of the heating circuit increased. Inversely, the duty cycle is small, consequently result in the power of heating circuit reduced until the detected temperature value equals to the nominal value, and thereby achieved automatic control purpose.

Hardware Design

MCU (Microchip)

The system adopts PIC16F877 as its CPU. The PIC Microcontroller made by the Microchip Technology Inc. applies the pipeline structure possessing simplify instruction set (RISC), the Harvard bus structure, two-grade instruction set and has high rate of capability-price, high speed, low voltage and power, and high power of output or input to drive LED directly (Sink current can reach 25 mA).

Field Temperature Collecting

As shown in FIGS. 6 and 7, the field temperature is collected by the temperature sensor. The system uses the MLX 90614 module which is very easy to utilize as the temperature sensor (Manufactured by the Melexis Inc.). All modules are verified in the factory and can give linear or sub-linear output. The modules have good ability of interchange and don't need the complex calibration.

LCD Display Circuit

During the process of heating, the LCD Display Circuit can display the parameters including the actual temperature, the target temperature set by user. The LCD display circuit uses the LM0321 chip manufactured by Hitachi Inc. The connection details with PIC16F877 are shown in FIG. 7.

Heating Drive Circuit

The circuit uses infrared bulb as heater which is AC220V and 100 W. The wavelength of the heater X1 covers the whole range of IR. As its highest output capacity is 40 mA, the I/O output terminal of the PIC16F877 can not drive the heater directly, and an isolation drive circuit must be used to achieve that MCU control the status of the power equipment. In the practical operation, a relay or a contractor is used to achieve the indirect driving. As the contractor and the relay are mechanical contact that largely lower the stability and reliability of the entire system. So, in order to avoid the demerit of mechanical switch, system utilized a full optical-electric isolated drive circuit with SCR as mainstay. SCR is switching mode with high power semiconductor component, worked under high voltage and big current condition; it has the advantages of small dimension, mechanical contact free and easy to fix. The details of heating drive circuit are shown in FIG. 6.

PIC16F887 will calculate the effective control value base on the field temperature, target temperature set by the user and the related parameters, and write this data to register of the MCU's timer 1 to calculate the duty cycle of the PWM. In the period of high level of PWM's wave, the bi-directional optical coupler U2 enabled, the grid of the Triac D1 will be triggered and become conducted, the heating circuit engaged. During the low level of PWM's wave, the bi-directional optical coupler U2 closed, without the trigger signal, the Triac D1 will cut-off and the heating circuit will stop working.

The R3 and C2 of the circuit consist of the capacitance-resistance unit. The purpose of this unit is to reduce the shock to the semiconductor continued rectifier (SCR) caused by self-induced electromotive force generated from the inductive component of the heating circuit when being shutdown. The R1 and R2 consist of the low-pass filters unit, which is to reduce the impact on the circuits generated by the faulty trigger of the bi-directional optical coupler. Meanwhile, the use of bi-directional optical coupler thoroughly isolates the high-voltage circuits and low-voltage circuits, and avoid interferes which the high power components made to MCU.

Design of the Software

The program of the system consists of several subsystems which including main program, temperature collection subprogram, heat control subprogram, keyboard scan subprogram, disconnection subprogram and etc. The function of the main program is to initialize and to self-test the components in the heating control system. It also can adjust the functional modules during the process of actual measurement. During the external interrupting and timer overflowing, the keyboard scanning and control algorithm subprograms can carry out the above-mentioned tasks using its plentiful interrupting resource of the PIC.

We claim:

1. A controllable infrared bio-effect system includes a shell (16), which contains an infrared source (1), the first group of filter mounting plate (2), convex lens (3), and concave lens (4), a second group of filter mounting plate (5), cable receptor device (6) and execution end (18); the first group of filter mounting plate (2) and the second group of filter mounting plate (5) are in line with a central axis, the convex lens (3) is installed between the infrared source (1) and concave lens (4); the first group of filter mounting plate (2) and the second group of filter mounting plate (5) are located between the concave lens (4) and the cable receptor device (6); the second group of filter mounting plate (2) is installed with a first filter (23); the second group of filter mounting plate (5) is installed with a second filter (7); the first filter (23) is in the same axis with the second filter (7); the first group of filter mounting plate (2), convex lens (3), concave lens (4), and second group of filter mounting plate (5) are parallely installed; an output end of the cable receptor device (6) is through the cable (8) and connected with the execution end (18); the first filter (23) is to filter UV rays and visible lights emitted by the infrared source (1); the concave lens (4) is to make parallel the spotted IR beam by the convex lens (3); the second filter (7) is used to receive a desired wavelength of infrared radiation; the cable receptor device (6) is to receive a beam emitted form the second filter (7), and transmit the beam to the execution end (18) through the cable (8).

2. The controllable infrared bio-effect system described in claim 1, the invention is characterized by installing a third filter (9) in the second group of filter mounting plate (5); an optical channel (24) is installed in the first group of filter mounting plate (2); the optical channel (24) is in the same axis with the third filter (9); the third filter (9) is used to receive the desired wavelength of infrared radiation emitted form the source (1); the cable receptor device (6) is used to receive the beam, and transmit the beam to the execution end (18) through the cable (8).

3. The controllable infrared bio-effect system described in claim 1, the invention is characterized by installing two parallel binary lenses A (10) and B (11); the two binary lenses A (10) and B (11) are installed in the second group of filter mounting plate (5) in an angle of 45°, respectively; install an optimal channel B (13) in the place opposite to the binary lens B (11) on the second group of filter mounting plate (5); install a fourth filter (25) in the first group of filter mounting plate (2); the fourth filter (25) is fixed in the same axis with the binary lens A (10); the binary lens B (11) receives the beams emitted from the concave lens (4) and the fourth filter (25), and then the produced beam is transmitted to the cable receptor (6) through the binary lens B (11) and the optimal channel (13).

4. The controllable infrared bio-effect system described in claim 3, the invention is characterized by equipping with a control system; the control system includes a CPU, a display part, a drive and a temperature signal collector (19); the temperature signal collector (19) is adapted with the execution end (18); the output port of the CPU is connected with the input port of the display; the output port of the CPU is connected with the output port of the infrared source (1); the port of the temperature signal collector (19) is connected with the port of the CPU; the temperature signal collector is used to collect the temperature signals and related data, then send them back to the CPU; the drive is used to drive the infrared source (1).

5. The controllable infrared bio-effect system described in claim 4, the invention is characterized by a drive motor (14) and a rack (20) which are fixed inside the shell (16) of the invention; a driven wheel (15) is fixed in the axis between the first group of filter mounting plate (2) and the second group of filter mounting plate (5); the first and second group of filter mounting plates (2) and (5) can rotate around the rack; the output axis of the drive motor (14) is connecting with the driven wheel (15).

6. The controllable infrared bio-effect system described in claim 4, a fan (17) is fixed inside of the shell (16).

7. The controllable infrared bio-effect system described in claim 5, the vent(s) (21) on the execution end (18) are in retractable structure.

8. The controllable infrared bio-effect system described in claim 3, the transmission rates of binary lenses A (10) and B (11) are greater-than-or-equal to 85% when the wavelength of IR transmitting the lenses is from 1400 nm to 2500 nm; the transmission rates of binary lenses A (10) and B (11) are lesser-than-or-equal to 5% when the wavelength of IR transmitting the lenses is from 800 nm to 1300 nm.

9. The controllable infrared bio-effect system described in claim 1, the transmission rates of the second filter (7) are greater-than-or-equal to 85% when the wavelength of IR transmitting the lenses is from 1600 nm to 2600 nm; the transmission rates of the second filter are greater-than-or-equal to 85% when the wavelength of IR transmitting the lenses is from 1400 nm to 2500 nm.

10. The controllable infrared bio-effect system described in claim 2, the transmission rate of the third filter (9) is greater-than-or-equal to 85% when the wavelength of IR transmitting the lenses is from 3000 nm to 5000 nm; the transmission rate of the third filter is lesser-than-or-equal to 5% when the wavelength of IR transmitting the lenses is from 200 nm to 2700 nm.

11. The controllable infrared bio-effect system described in claim 2, the invention is characterized by installing two parallel binary lenses A (10) and B (11); the two binary lenses A (10) and B (11) are installed in the second group of filter mounting plate (5) in an angle of 45, respectively; install an optimal channel B (13) in the place opposite to the binary lens B (11) on the second group of filter mounting plate (5); install a fourth filter (25) in the first group of filter mounting plate (2); the fourth filter (25) is fixed in the same axis with the binary lens A (10); the binary lens B (11) receives the beams emitted from the concave lens (4) and the fourth filter (25), and then the produced beam is transmitted to the cable receptor (6) through the binary lens B (11) and the optimal channel (13).

12. The controllable infrared bio-effect system described in claim 11, the invention is characterized by equipping with a control system; the control system includes a CPU, a display part, a drive and a temperature signal collector (19); the temperature signal collector (19) is adapted with the execution end (18); the output port of the CPU is connected with the input port of the display; the output port of the CPU is connected with the output port of the infrared source (1); the port of the temperature signal collector (19) is connected with the port of the CPU; the temperature signal collector is used to collect the temperature signals and related data, then send them back to the CPU; the drive is used to drive the infrared source (1).

13. The controllable infrared bio-effect system described in claim 12, the invention is characterized by a drive motor (14) and a rack (20) which are fixed inside the shell (16) of the invention; a driven wheel (15) is fixed in the axis between the first group of filter mounting plate (2) and the second group of filter mounting plate (5); the first and second group of filter mounting plates (2) and (5) can rotate around the rack; the output axis of the drive motor (14) is connecting with the driven wheel (15).

14. The controllable infrared bio-effect system described in claims 12, a fan (17) is fixed inside of the shell (16).

15. The controllable infrared bio-effect system described in claim 13, the vent(s) (21) on the execution end (18) are in retractable structure.

16. The controllable infrared bio-effect system described in claim 11, the transmission rates of binary lenses A (10) and B (11) are greater-than-or-equal to 85% when the wavelength of IR transmitting the lenses is from 1400 nm to 2500 nm; the transmission rates of binary lenses A (10) and B (11) are lesser-than-or-equal to 5% when the wavelength of IR transmitting the lenses is from 800 nm to 1300 nm.

\* \* \* \* \*